United States Patent [19]

Leonard

[11] Patent Number: 5,026,999
[45] Date of Patent: Jun. 25, 1991

[54] METHOD OF REMOTELY MEASURING SUBSURFACE WATER TEMPERATURES BY STIMULATED RAMAN SCATTERING USING STIMULATED BRILLOUIN BACKSCATTERING

[75] Inventor: Donald A. Leonard, Cupertino, Calif.

[73] Assignee: GTE Government Systems Corporation, Stamford, Conn.

[21] Appl. No.: 506,304

[22] Filed: Apr. 9, 1990

[51] Int. Cl.$^5$ .............................. G01J 5/48; G01J 3/44
[52] U.S. Cl. ..................................... 250/574; 356/301; 356/43; 374/136; 374/161
[58] Field of Search ................. 356/43, 301, 318, 342; 250/574, 231.1; 374/121, 127, 136, 137, 161, 131

[56] References Cited

U.S. PATENT DOCUMENTS

| | | | |
|---|---|---|---|
| 3,986,775 | 10/1976 | Chang | 356/301 |
| 4,123,160 | 10/1978 | Caputo et al. | 356/301 |
| 4,767,219 | 8/1988 | Bibby | 356/301 |
| 4,867,564 | 9/1989 | Sweeney et al. | 356/43 |
| 4,986,655 | 1/1991 | Sweeney et al. | 356/301 |
| 4,986,656 | 1/1991 | Sweeney et al. | 356/301 |

OTHER PUBLICATIONS

Vladimir V. Shjunov et al., "Optical Phase Conjugation", *Scientific American*, Dec. 1985, pp. 54-59.
David M. Pepper, "Applications of Optical Phase Conjugation", *Scientific American*, Jan. 1986, pp. 74-83.
B.Ya. Zel'dovich, N. F. Pilipetsky, V. V. Shkunov, "Principles of Phase Conjugation", Springer-Verleg, vol. 42, p. 29, Springer Series on Optical Sciences (Springer Verlag Berlin Heidelberg, 1985).

*Primary Examiner*—David C. Nelms
*Assistant Examiner*—Michael Messinger
*Attorney, Agent, or Firm*—James J. Cannon, Jr.; John F. Lawler

[57] ABSTRACT

A technique for measuring the unknown subsurface temperature T of a bulk transparent medium such as sea water by focussing a high intensity pulsed laser beam in a first direction into the water to a predetermined depth D, producing stimulated Brillouin scattering (SBS) in a second direction opposite to the first direction and generating from the SBS stimulated Raman scattering (SRS) in the second direction, analyzing the spectra of the SRS and determining therefrom the temperature T. The depth D is is selected to insure that the entire SBS pulse is in the water.

5 Claims, 7 Drawing Sheets

METHOD OF REMOTELY MEASURING SUBSURFACE WATER TEMPERATURES BY STIMULATED RAMAN SCATTERING USING STIMULATED BRILLOUIN BACKSCATTERING

RELATED APPLICATIONS

"APPARATUS FOR AND METHOD OF REMOTELY SENSING SUB-SURFACE WATER TEMPERATURES," U.S. Pat. No. 4,867,564, issued Sept. 19, 1989.

"METHOD OF REMOTELY DETECTING SUBMARINES USING A LASER," U.S. Pat. No. 4,867,558, issued Sept. 19, 1989.

"REMOTE SUBSURFACE WATER TEMPERATURE MEASURING APPARATUS WITH BRILLOUIN SCATTERING," Ser. No. 387,735, filed Aug. 1, 1989, now U.S. Pat. No. 4,498,958.

"REMOTE SUBSURFACE HATER TEMPERATURE MEASURING APPARATUS," Ser. No. 386,383, filed July 28, 1989, now U.S. Pat. No. 4,973,853.

"REMOTE SUBSURFACE WATER TEMPERATURE MEASURING APPARATUS," Ser. No. 400,217, filed Aug. 29, 1989, now U.S. Pat. NO. 4,962,319.

"METHOD FOR OPTICALLY AND REMOTELY SENSING SUBSURFACE WATER TEMPERATURE," Ser. No. 387,734, filed Aug. 1, 1989, now U.S. Pat. No. 4,984,903.

BACKGROUND OF THE INVENTION

This invention relates to the remote measurement of the properties of transparent media, such as the measurement of subsurface ocean temperature profiles from aircraft and surface and subsurface vessels, and in particular to an improved method of making such measurements.

Remote sensing of the ocean and the atmosphere is being used increasingly in on-line environmental surveillance. An example of such remote sensing is the measurement of subsurface ocean water temperatures for enhancement of acoustic surveillance. However, the method of non-linear spectroscopy, such as stimulated Raman scattering (SRS), has not in general been applied for this purpose in spite of its well-known advantages of better spectral resolution and higher signal to noise ratio that have been observed in laboratory experiments.

A major difficulty of applying SRS to the above remote sensing needs has been the requirement for the laser source and the receiver to be at opposite sides of the investigated medium. SRS normally occurs in the same direction as the incident laser beam which would preclude single-ended remote sensing as occurs, for example, in subsurface ocean temperature mapping from an aircraft.

This invention s directed to a method which overcomes such difficulties in using SRS in these investigations.

OBJECTS AND SUMMARY OF THE INVENTION

A general object of the invention is the provision of a new method of operating a bulk scattering laser radar which employs a combination of Brillouin and Raman scattering.

A more specific object is the provision of a method of remotely measuring physical characteristics, such as subsurface temperature, of ocean water with higher sensitivity and a lower signal-to-noise ratio.

Still another object is the provision of such a method using stimulated Raman scattering (SRS) in which the laser source and the receiver are on the same side of the medium being investigated.

These and other obJects of the invention are achieved by directing into the medium being investigated a pulsed laser beam having an intensity sufficient to produce stimulated Brillouin scattering (SBS) pulses in the medium propagating backwardly toward the source of the laser beam, increasing the intensity of the SBS pulses sufficiently to generate SRS pulses in the same direction in the medium as the SBS pulses, separating the SBS and SRS pulses, and optically analyzing the SRS pulses to determine the unknown characteristics of the medium.

DESCRIPTION OF PREFERRED EMBODIMENT

Figure 1:
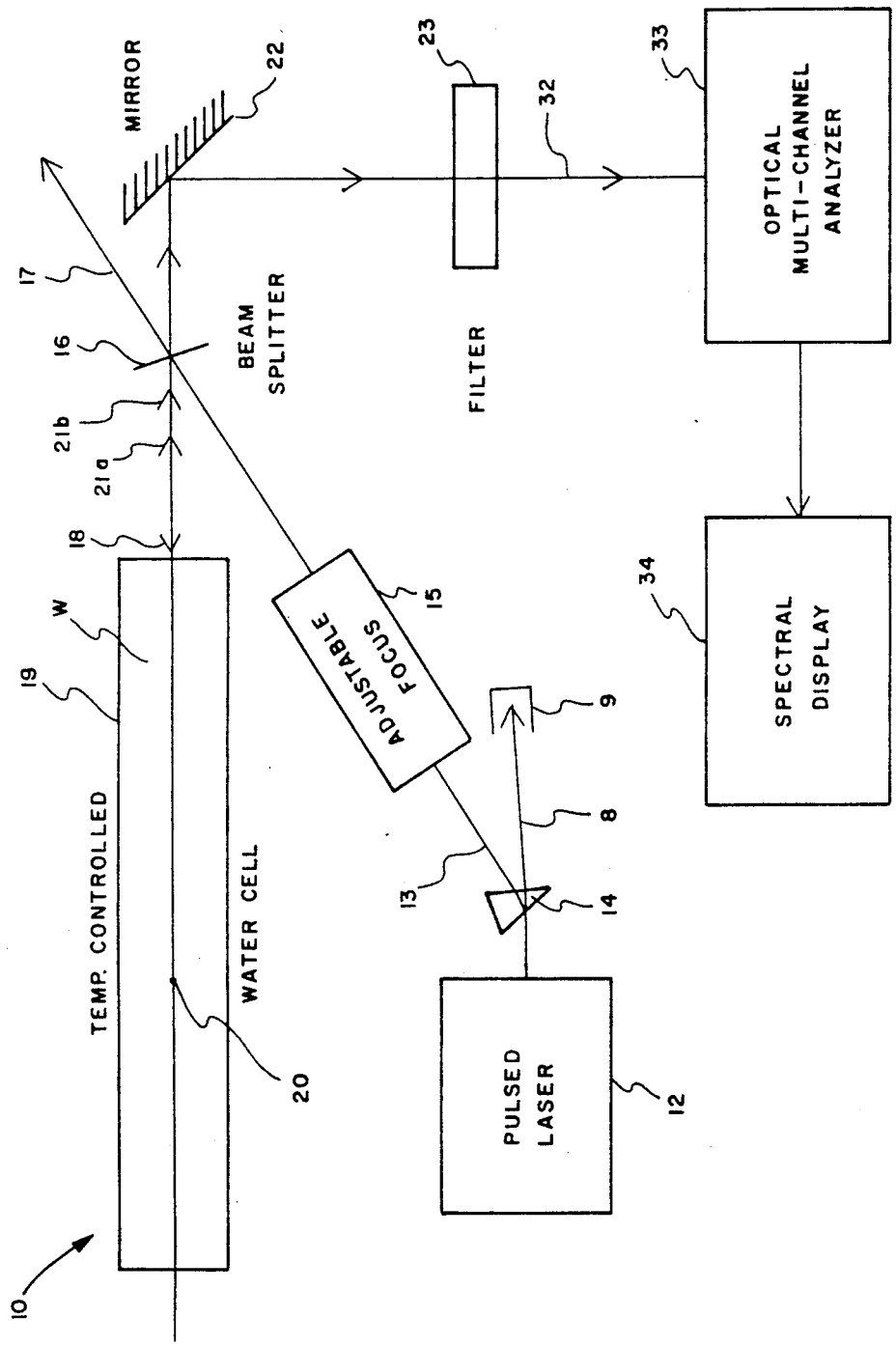
FIG. 1 is a schematic diagram of apparatus used in the practice of the invention.

Referring now to the drawings, FIG. 1 shows apparatus 10 with which the invention is practiced comprising a pulsed laser 12, such as a frequency-doubled neodymnium yttrium-aluminum-garnet (Nd:YAG) laser, the frequency-doubled output 13 of which is directed by prism 14 through an adjustable focus device 15, such as a telescope, to a beam splitter 16 consisting of a partially-transmissive partially-reflective mirror. The fundamental frequency output 8 of laser 12 is directed by prism 14 to a beam dump 9. Splitter 16 divides beam 13 into a first sub-beam 17 which passes through splitter 16 and a second sub-beam 18 which is reflected thereby into a sample of the medium being investigated. This medium is shown as a temperature-controlled cell 19 of water H which simulates ocean water or the like.

Device 15 adjustably focusses sub-beam 18 to a focal point 20 in cell 19. The unknown temperature of interest is the temperature of medium 19 at or near focal point 20.

When intensity of the pulsed laser frequency--doubled output beam 13 exceeds a predetermined threshold level, sub-beam 18 produces stimulated Brillouin scattering in cell 19 resulting in the generation of a phase-conjugate or "time-reversed" beam 21a whose ray runs along the same trajectory as, but in the opposite direction to, sub-beam 18. This phenomenon, called optical phase conjugation, is well known and is described in detail in articles entitled "Optical Phase Conjugation" by V. V. Shkunov et al, Scientific American, pages 54-59 (September 1985) and "Applications of Optical Phase Conjugation" by D. M. Pepper, Scientific American, pages 74–83 (January 1986).

In accordance with this invention, the intensity of laser output beam 13 is increased to such a level that sub-beam 18 produces in cell 19 an SBS beam 21a at a sufficiently high intensity level that an SRS beam 21b travelling in the same or backward direction so that both the SBS and SRS components appear as coincident output beams 21a and 21b from cell 19. Generation of the SRS component 21b in cell 19 is accomplished by increasing the intensity of the laser output 13 which shortens the width and raises the intensity of the SBS output pulses 21a until their intensity reaches and exceeds the threshold level at which SRS is produced. The SRS pulse derives its energy from the SBS pulse and accordingly laser output pulses 13 must be focussed sufficiently deeply into the medium H that the whole or most of the resulting SBS pulses are wholly contained in the medium and thus are available to transfer maximum energy to the SRS process SBS pulses are in the green part of the spectrum and SRS pulses are in the red portion.

In order to achieve SBS, a predetermined threshold intensity level for the optical probe beam 13 must be exceeded. This intensity level must be sufficient so that the following relationship exists:

$$\exp[GIL] \geq 10^{13}$$

or, $$\exp[GIL] \geq \exp[30],$$

(since $10^{13} = \exp[30]$).

Or more simply, the intensity, $I \geq 30/GL$, where,
G = a gan parameter which is a property of the medium, m/H
I = intensity of the optical probe beam (H/m$^2$) and,
L = interaction length, m,
see "Principles of Phase Conjugation" by Zel'dovich et al., Springer-Verlag, Vol. 42, page 29, Springer Series on Optical Sciences (Springer Verlag Berlin Heidelberg, 1985). (For water G is typically $5 \times 10^{-11}$ m/W.)

In order to achieve SRS, the intensity of the probe beam needs to be a factor of 10 to 20 greater than the minimum for the threshold of the SBS pulses. Tests in the laboratory have shown that with an SBS threshold of 2mJ, a probe beam intensity increase to the range of 20 to 40 mJ is required before reliable SRS conversion is observed.

Figure 2:
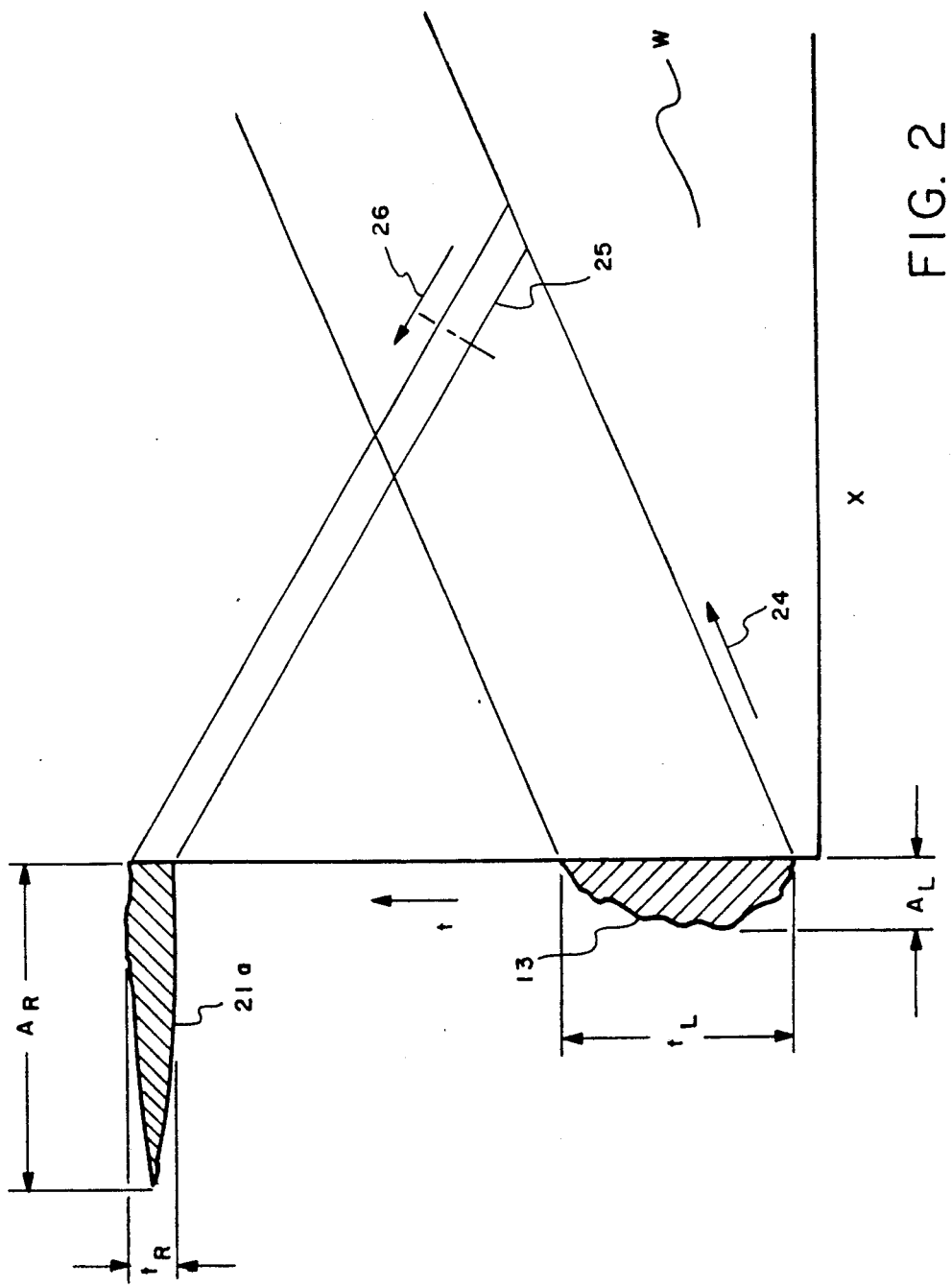
FIG. 2 is a time-distance diagram depicting the interaction of an SBS pulse with the investigated medium in accordance with the invention and the SRS pulse resulting from such interaction.

In order to better understand the process on which this invention is based, reference is made to the t-x diagram in FIG. 2 which shows distance or "x" as the abscissa and time or "t" as the ordinate. The laser output pulse 13 having a width $t_L$ and an amplitude $A_L$ is transmitted into the water sample W in the direction of the arrow 24 as shown As the amplitude AL of laser pulse 13 reaches a magnitude sufficient to produce SBS, an SBS pulse forms at 25 and propagates in the direction of arrow 26 which in fact is opposite to direction 24. On the x-t plot, the slope of arrow 26 is equal in magnitude but opposite in sign to the slope of arrow 24. As the intensity of laser pulse 13 increases sufficiently to reach the threshold for SBS pulse formation at 25, the latter propagates in the direction of arrow 26 and appears at the surface of the water W as pulse 21a. Pulse 21a has an amplitude $A_R$ substantially greater than $A_L$ of laser pulse 13 and a width $t_R$ considerable narrower than that of pulse 13. As the intensity of laser pulse 13 is continually increased, the amplitude $A_R$ of the SBS pulse 21a continues to increase. At some value of $A_R$ the threshold for the production of SRS is exceeded and an SRS pulse 21b is produced which travels in the same direction as pulse 21a.

The output beams 21a and 21b from medium 19, see FIG. 1, pass through splitter 16 and are reflected by mirror 22 to filter 23 which passes the desired signals as described below and blocks the rest.

Figure 3:
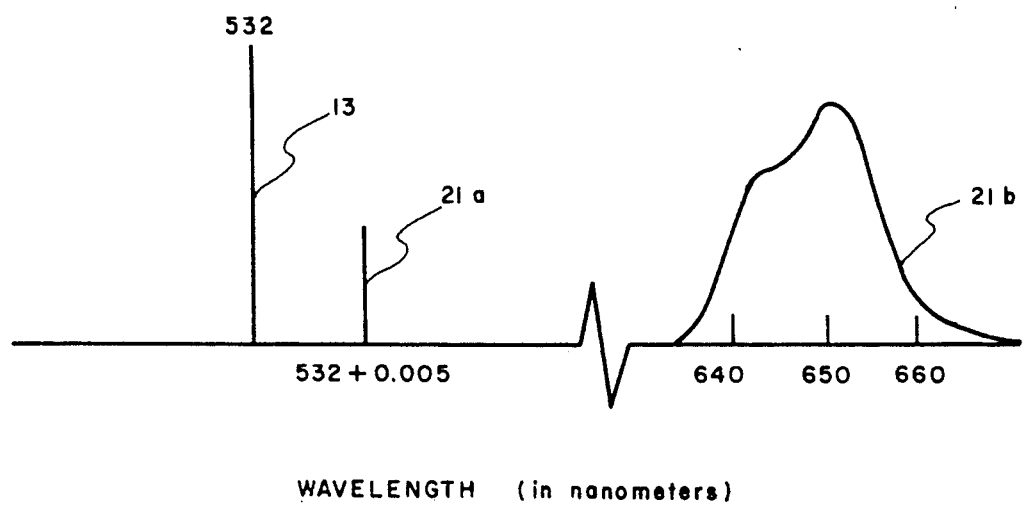
FIG. 3 is a frequency spectrum diagram showing representative spectra of backscattered signals and the laser probe beam signal.
Figure 4A:
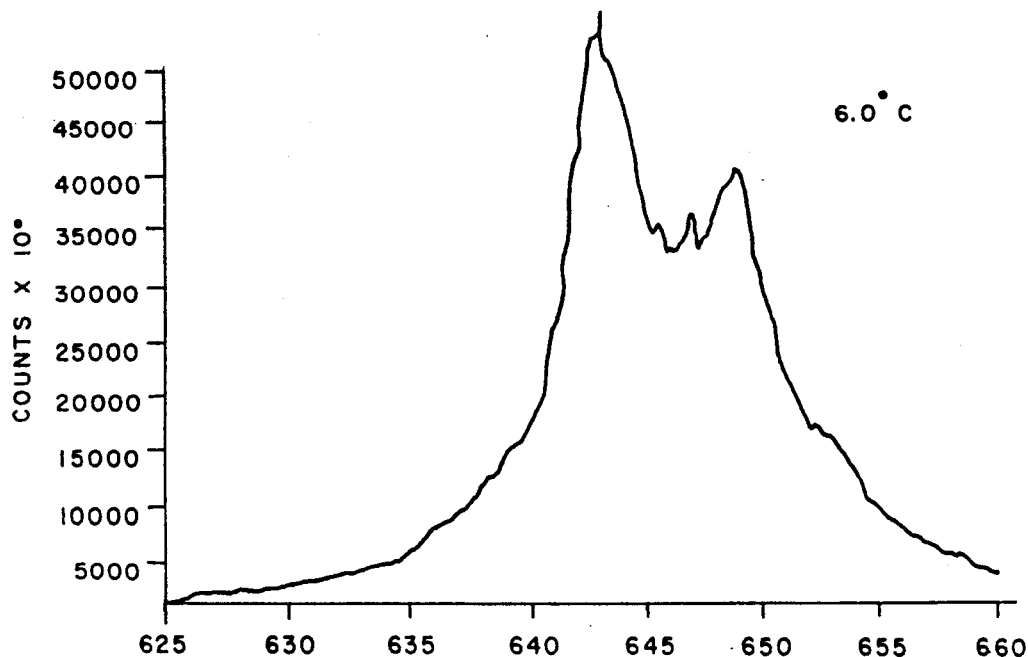
FIGS. 4a, 4b, 4c, 4d, 4e, and 4f are spectral record of the SRS pulses received from water samples at six different temperatures in accordance with this invention.
Figure 4B:
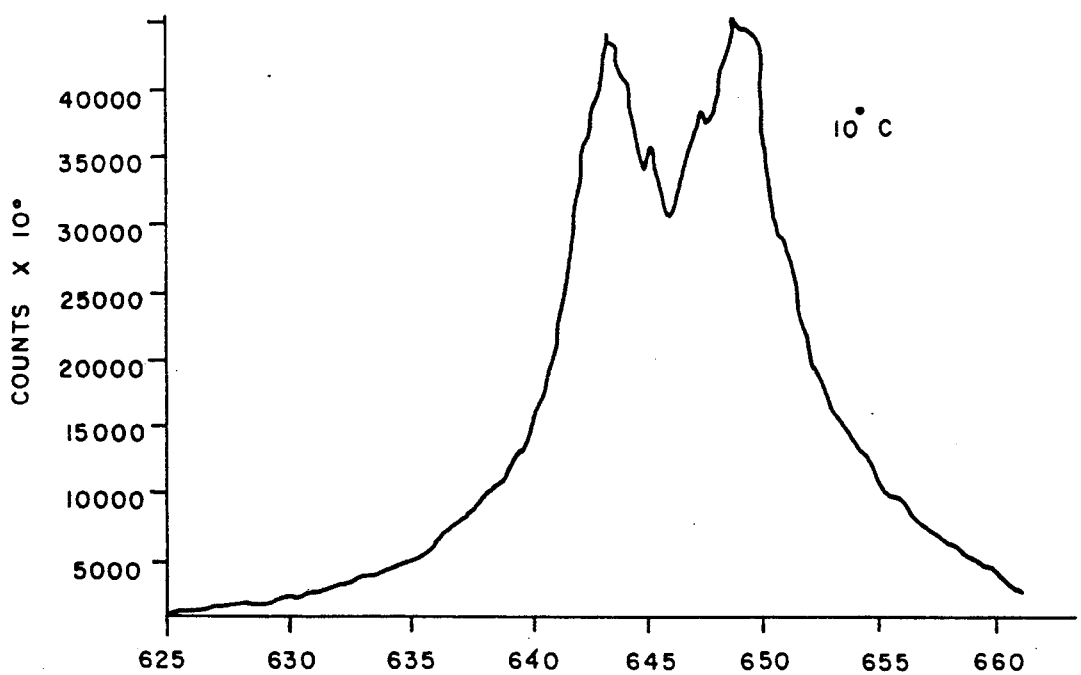
Figure 4C:
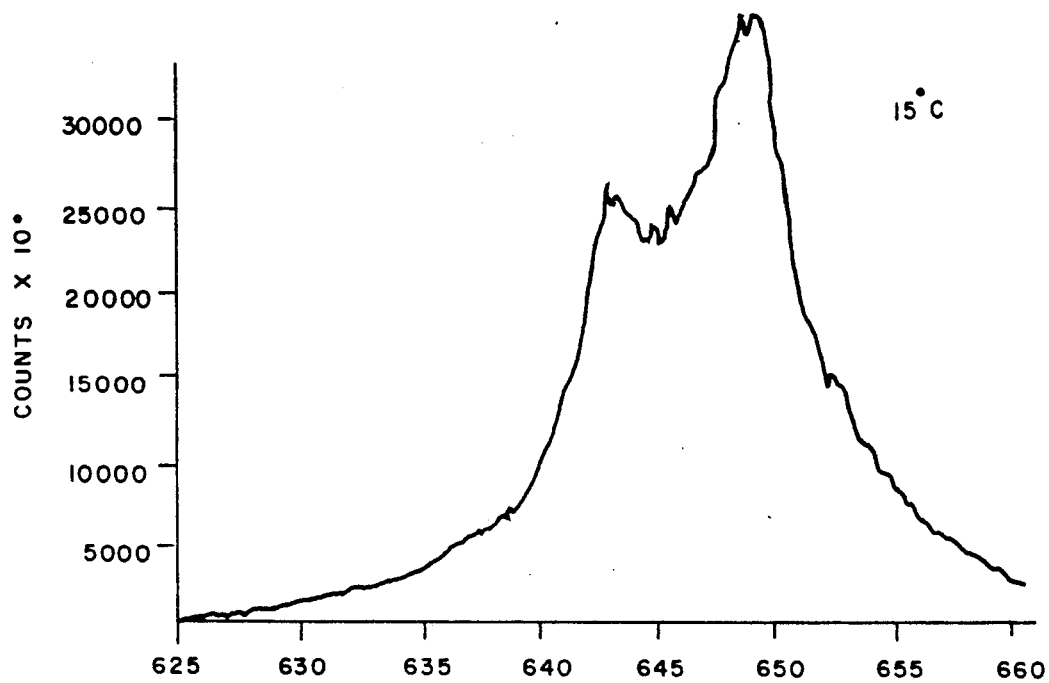
Figure 4D:
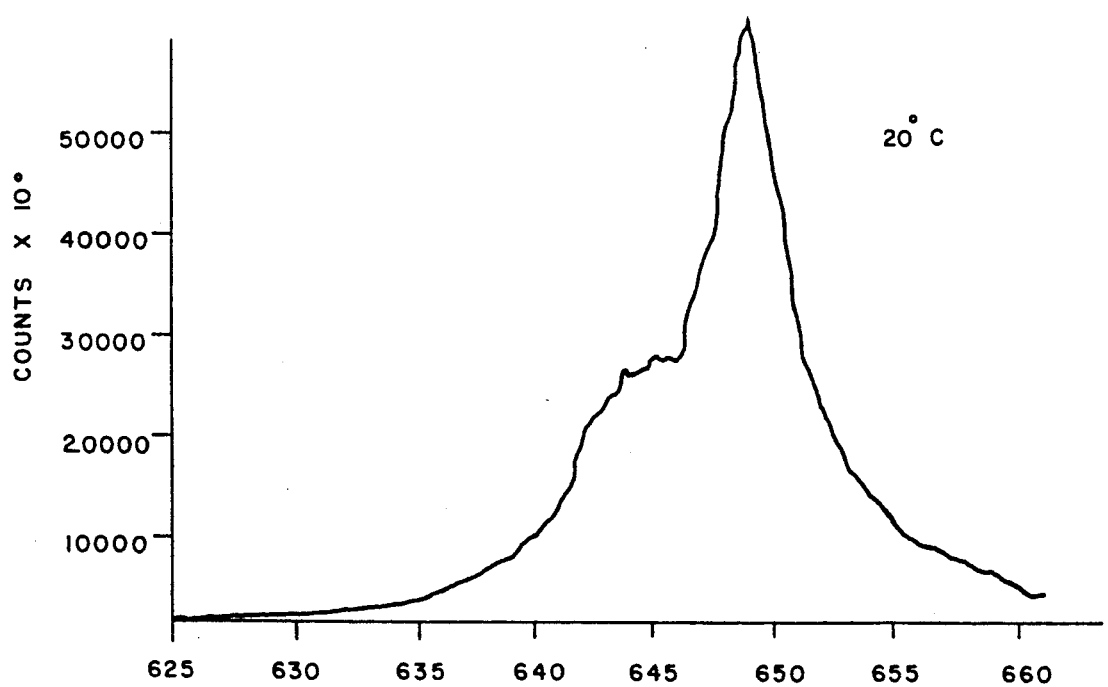
Figure 4E:
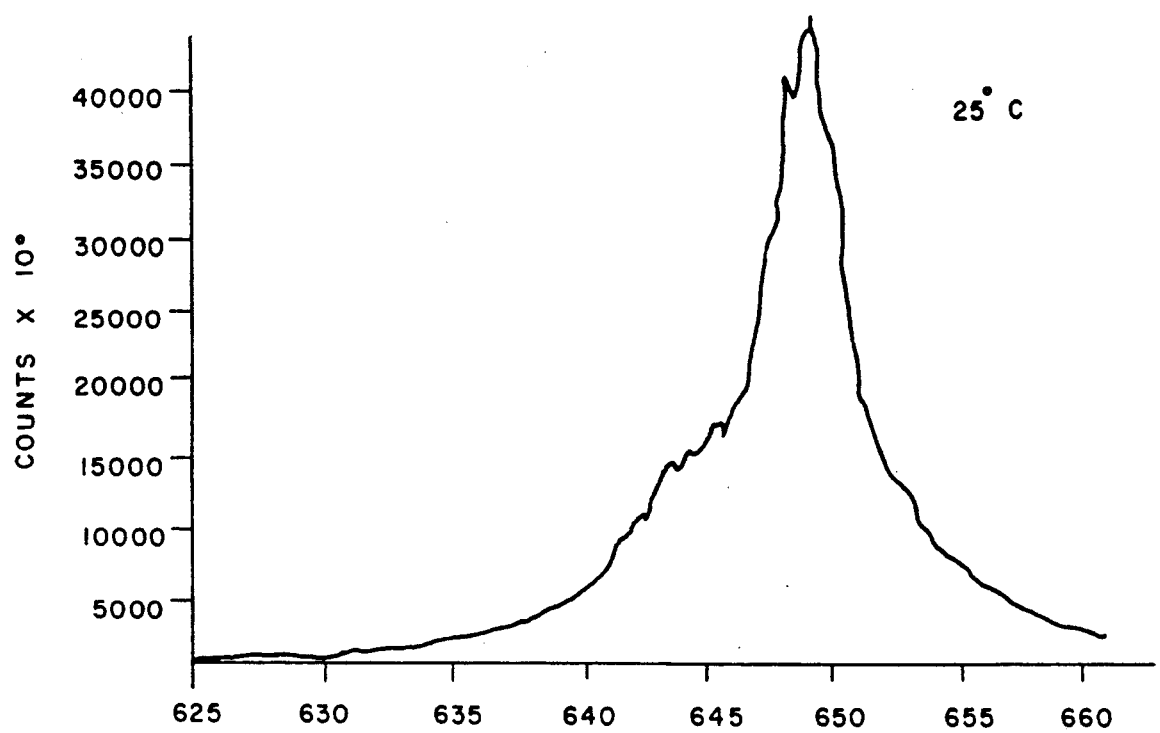
Figure 4F:
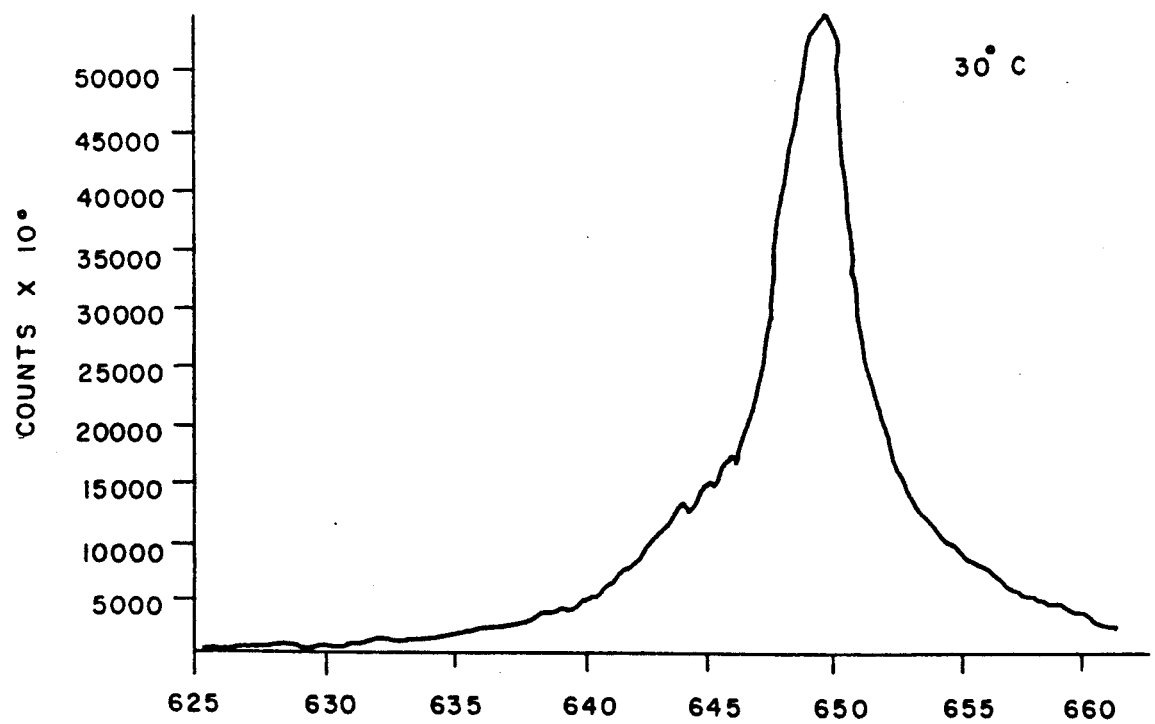

FIG. 3 depicts the wavelength distribution of a laser output or probe beam signal 13 at a wavelength of 532 nanometers and the SBS and SRS signals 21a and 21b, respectively. These signals appear at the input to filter 23 (FIG. 1) which blocks probe beam signal 13 and SBS signal 21a (green) so that only SRS signal 21b (red) appear at output 32 of filter 23. Output 32 is passed to an optical multichannel analyzer 33, the output of which is fed to a spectral display device 34. Analyzer 33 may be a spectrometer with an imaging focal plane manufactured by EG&G/Princeton Applied Research, Princeton, New Jersey, and device 34 may be a cathode ray tube.

Spectra of the Raman beam, from 625 to 660 nm, was obtained on display device 34 for water temperatures of 6, 10, 15, 20, 25 and 30° C., each spectrum comprising a 100 pulse average. These spectra are shown in FIG. 4(a)–4(f), respectively, wherein the abscissa in each is wavelength in nanometers and the ordinate is relative intensity. It can be seen from these spectral recordings that a very obvious and distinct change in the character of the spectra occurs as a function of temperature. The spectra are double peaked but the ratio of the peaks changes with temperature, the long wavelength peak becoming greater as the temperature increases.

Figure 5:
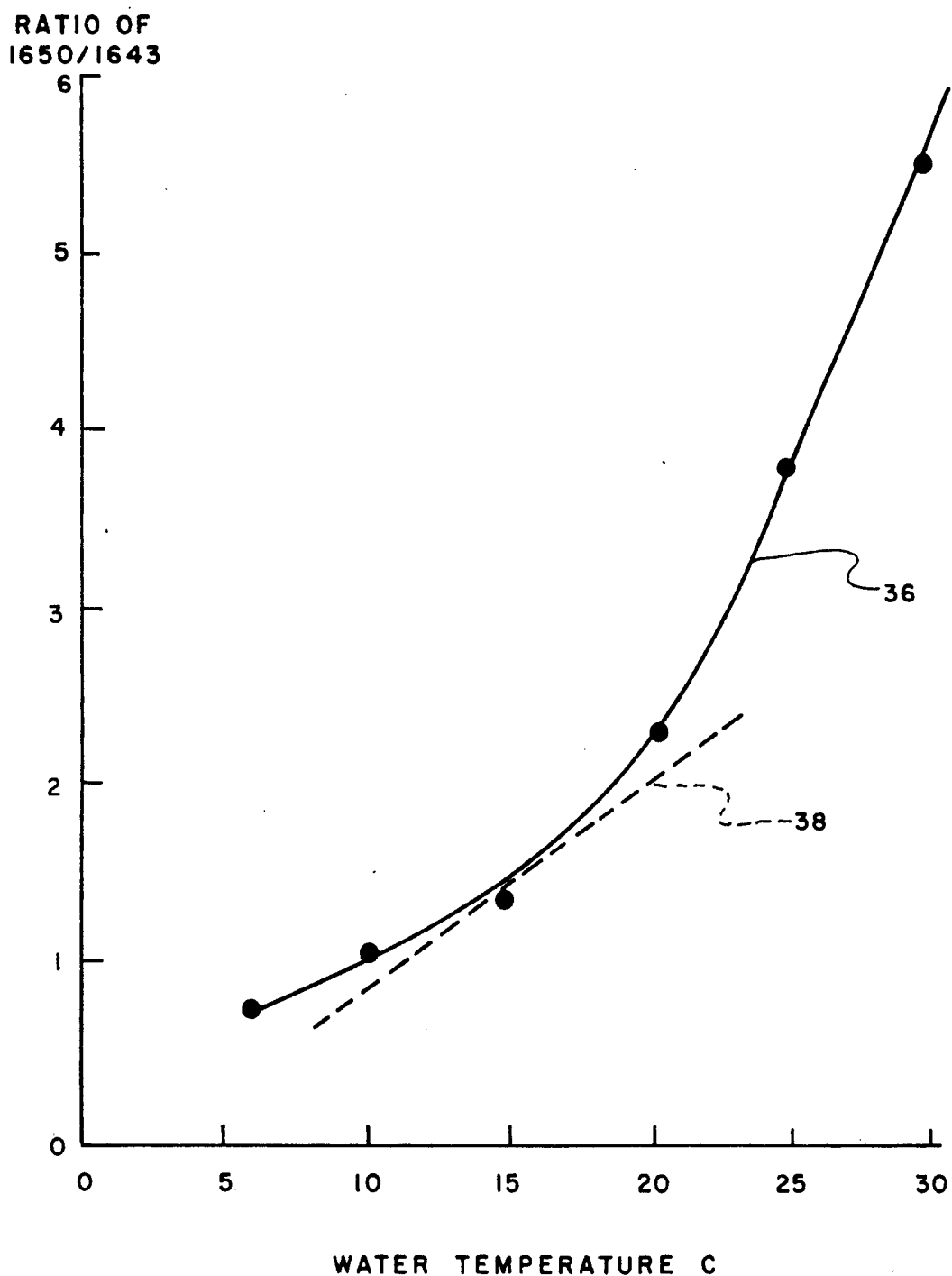
FIG. 5 is a plot showing the ratio of the intensity of SRS pulses at two different wavelengths as a function of temperature of the medium for each spectrum shown in FIG. 4.

FIG. 5 shows a plot 36 which depicts the ratio of the intensity at 650 nm to the intensity at 643 nm as a function of the temperature of the water for each spectrum. The ratio is seen to increase from a value of 0.7 at 6° C. to a value of 5.5 at 30° C. Of great significance is the slope efficiency of this plot, shown by the broken line 38, which is the sensitivity of the measurement. Line 38 shows that at a temperature of 15° C., for example, the ratio changes by 10% for a 1° C. change in temperature. This is an order of magnitude higher than the sensitivity for prior art spontaneous Raman scattering which exhibits a sensitivity of about 1% per °C, see the article entitled "Raman Spectral Studies of the Effect of Temperature on Water Structure" by G. E. Halrafen, Journal of Chemical Physics, Vol. 47, pages 114–126 (1967). The practical consequence of this result is that a given temperature sensitivity can be achieved with SRS signals, with a receiver that is operating with 10 dB lower signal-to-noise ratio than would be required if spontaneous Raman scattering were used. These results demonstrate for the first time a new mode of operation of a bulk laser scattering radar employing a combination of Raman and Brillouin scattering, the sensitivity of 10% per degree being about an order of magnitude higher than the usual sensitivity of 1% per degree that is obtained with spontaneous Raman scattering.

What is claimed is:

1. The method of remotely measuring temperature a medium with a pulsed laser consisting of the steps of:
    directing the output of said laser in a first direction into a body of said medium;
    increasing the intensity of said laser output pulses to a value sufficient to produce in said medium stimulated Brillouin scattering (SBS) pulses in a second direction opposite to said first direction;

increasing the intensity of said SBS pulses sufficiently to produce stimulated Raman scattering (SRS) pulses in said second direction in said water; and analyzing said SRS pulses and thereby producing a spectral record indicative of temperature of the medium.

2. The method according to claim 1 in which the intensity of the laser output pulses is increased by raising the output power of said laser.

3. The method according to claim 1 in which the intensity of the laser output pulses is increased by decreasing the width of the laser output pulses.

4. The method according to claim 1 in which the laser output is focussed sufficiently deeply into said medium that the resulting SBS pulses are substantially wholly contained in the medium.

5. The method of remotely measuring temperature of water with a pulsed laser consisting of the steps of:

focussing the output of said laser in a first direction into a body of said water;

increasing the intensity of said laser output pulses to a value sufficient to produce in said water stimulated Brillouin scattering (SBS) in a second direction opposite to said first direction;

adjusting the depth D of focussing of the laser output into the water to a magnitude sufficient to enable substantially the entire SBS pulse to be contained in the water;

increasing the intensity of said SBS pulses sufficiently to produce stimulated Raman scattering (SRS) pulses in said second direction in said water;

passing said SBS and SRS pulses through a filter to remove all but said SRS pulses; and analyzing said SRS pulses and thereby producing a spectral record indicative of the temperature of the water.

* * * * *